United States Patent
Good et al.

Patent Number: 5,336,248
Date of Patent: Aug. 9, 1994

[54] TREATMENT AND INHIBITION OF RETINOPATHY OF PREMATURITY

[75] Inventors: Peter A. Good, Birmingham; Christopher J. Morris, Sutton Coldfield; Andrew W. D. Claxson, London; David R. Blake, Droitwich, all of England

[73] Assignee: British Technology Group Ltd., London, England

[21] Appl. No.: 778,916

[22] PCT Filed: Jul. 18, 1990

[86] PCT No.: PCT/GB90/01101
§ 371 Date: Aug. 20, 1992
§ 102(e) Date: Aug. 20, 1992

[87] PCT Pub. No.: WO91/01158
PCT Pub. Date: Feb. 7, 1991

[30] Foreign Application Priority Data
Jul. 18, 1989 [GB] United Kingdom ............. 8916357

[51] Int. Cl.$^5$ ........................................ A61N 5/06
[52] U.S. Cl. ............................... 607/90; 607/88
[58] Field of Search ............ 128/857, 666; 600/21, 600/22; 607/90, 91, 94, 88; 359/464, 465, 466; 362/293, 339

[56] References Cited

U.S. PATENT DOCUMENTS

| | | | |
|---|---|---|---|
| 2,515,236 | 7/1950 | Kunins | 362/293 |
| 3,269,267 | 8/1966 | Collins | |
| 3,821,577 | 6/1974 | Larson | 607/88 |
| 3,877,437 | 4/1975 | Maitan et al. | 600/22 |
| 4,172,632 | 10/1979 | Holmes, Jr. | 359/465 |
| 4,411,263 | 10/1983 | Cook | |
| 4,444,190 | 4/1984 | Mutzhos | 607/94 |
| 4,750,474 | 6/1988 | Dukhan et al. | 600/22 |
| 5,243,460 | 9/1993 | Kornberg | 359/464 |

FOREIGN PATENT DOCUMENTS

| | | |
|---|---|---|
| 455071 | 6/1968 | Switzerland . |
| 269553 | 10/1927 | United Kingdom . |
| 2216012 | 10/1989 | United Kingdom . |

OTHER PUBLICATIONS

WO, A, 84/00693 (Schonberg) Mar. 1, 1984, see p. 5, lines 3–8; p. 6, line 18–p. 7, line 3; p. 11, line 25–p. 12, lines 43–58; FIG. 3.

*Primary Examiner*—Lee S. Cohen
*Assistant Examiner*—Brian M. Greer
*Attorney, Agent, or Firm*—Cushman, Darby & Cushman

[57] ABSTRACT

The present invention relates to an apparatus for the treatment of or the inhibition of retinopathy of prematurity and to a method for treating or for inhibiting retinopathy of prematurity. The apparatus provided in accordance with the present invention includes a component or system for providing substantially only red light. Thus, light is provided having a wave band of approximately 612 nm or more. Furthermore, at least the patient's head is received in a device that limits the light which reaches the patient's eyes to the aforementioned red light. Thus, the patient is allowed to see substantially only red light.

10 Claims, 2 Drawing Sheets

TREATMENT AND INHIBITION OF RETINOPATHY OF PREMATURITY

The present invention relates to the treatment and inhibition of retinopathy of prematurity (ROP).

BACKGROUND OF THE INVENTION

The care and treatment of severely premature babies has achieved a high degree of effectiveness, and further advances are to be expected. One important aspect of this care and treatment is in the control of the oxygen level of the air supplied to such babies at an elevated level. It has, however, been found that a high level of oxygen can lead to ROP. Careful control of the oxygen level is therefore required, but although this reduces the incidence of ROP, the need for a high oxygen level to maintain the general health of the baby means that there Is still an appreciable risk of ROP, a risk which rises to a high level for severe prematurity. Although there is substantially complete recovery of sight from ROP in most cases, it leads to complete blindness in a small but significant number of cases.

Premature babies may be exposed to high light levels, which may arise from a variety of causes such as sunlight, strong and continuous artificial ward light generally, and the use of phototherapy. There has been substantial speculation that the risk of ROP is increased by such exposure to high levels of light.

Phototherapy consists of exposing the baby to a high intensity white or short wavelength light for the treatment of neonatal jaundice (hyperbiliruminaemia). It is well known to "patch", i.e. blindfold, babies undergoing such treatment. The treatment lasts for periods in the region of 24 hours; patching may well reduce the chance of ROP developing, and is unlikely to have any harmful effects for that kind of length of time.

It has also been suggested that the general light intensity to which premature babies are subjected should be kept low, and an investigation has been carried out in which filters were placed over the incubators of certain premature babies, cutting the light intensity by about 50%. The results indicated that this reduced the incidence and severity of ROP. This investigation has, however, been criticized.

Studies have also been performed using animals, and some of the results of these also lend support to the view that high light levels damage the human eye. However, the precise relevance of these studies to ROP is unclear for a variety of reasons.

The general practice with premature babies is, therefore, to patch their eyes during phototherapy, but to take no further special measures to reduce the light levels to which they are exposed (though general awareness of the matter may result in a greater readiness to draw the curtains or blinds if there is strong sunshine into the ward, and caution when designing lighting systems for premature baby wards.

There have been no serious proposals to maintain premature babies in permanent darkness (either total body darkness or by patching). The major reasons for this are, probably, that total darkness makes it very difficult to monitor the baby; the effectiveness of permanent patching would be doubtful, as the blindfolds would be liable to become dislodged; parental dissatisfaction; and, of course, the well-known fact that, at least in certain animal species, exposure to light is essential for proper development of sight.

BRIEF DESCRIPTION OF THE INVENTION

We hypothesize that at least part of the mechanism of photic damage leading to ROP is similar to that causing certain other types of eye damage.

More specifically, we hypothesize that desferrioxamine (DFX) and oxygen toxicity of the retina are related. DFX has been used in the treatment of iron overload states, particularly thalassaemia, as it is a powerful chelator of iron and copper. It has however been found to cause eye damage. It is believed that this is because iron (or copper), in the presence of light and oxygen, is involved in the generation of oxygen free radical species, leading to lipid peroxidation. At least part of the retinal damage in premature babies exposed to hyperoxia has also been attributed to a lipid peroxidative process.

We have investigated the effect of light of various colours on dark-adapted albino rats to which DFX had been administered. Ne found that the electro-rettnogram (ERG) readings were severely depressed by continuous white light after 2 days, rising gradually thereafter (though still remaining well below normal at day 8). For yellow or cyclic white light, the initial depression was less severe, and the reading returned substantially to normal at 8 days. For continuous darkness, the depression was still less severe but still noticeable, and returned to normal at day 8. However, the readings for rats continuously exposed to red light were not significantly depressed.

These results suggest that eye damage involving free radicals and/or lipid peroxidation is increased by short wavelength light, but that red light has a protective effect against such damage and/or promotes recovery after such damage.

We also investigated the effect of light of various colours on dark adapted albino rats. He found that the ERG readings were progressively depressed by blue and white light, and at a lesser rate by yellow and orange light, but recovered when the rats were returned to darkness. However, the readings for rats continuously exposed to red light were not significantly depressed. He have found that the critical wavelength for this is approximately 612 nm. By "red" light, therefore, we mean light with a waveband extending substantially from approximately 612 nm upwards.

We believe that the use of red light is beneficial in the treatment and/or inhibition of retinopathy of prematurity.

Accordingly in one aspect the present invention comprises apparatus comprising means for providing substantially only red light for use in the treatment or inhibition of retinopathy of prematurity.

It will be appreciated that the means for providing light which is substantially only red will vary in accordance with the therapeutic context. Red light may be produced directly, from a red light source, or alternatively, a light filter material may be interposed between the eyes of a patient and a light source whereby the eyes are exposed only to red light.

Thus treatment can be effected by the patient wearing a suitable eye protector incorporating a red filter material. Premature babies are treated with particular convenience in an incubator or a headbox which is provided with lighting means and such that the baby is allowed to see substantially only red light or provided with light filter means restricting the light to which the baby Is exposed to substantially only red light. Typically the incubator or headbox, which may be provided with inlet means and outlet means for oxygen and optionally with means controlling the level of oxygen therein, comprises portions thereof e.g. transluscent panels which transmit substantially only red light.

The present Invention also comprises in a further aspect thereof a method for the Inhibition or treatment of retinopathy of prematurity which comprises allowing a subject (e.g. a premature baby) to see substantially only red light or restricting the light to which the subject is exposed to substantially only red light. The present Invention further comprises the manufacture of apparatus comprising means for providing substantially only red light as hereinbefore defined for use in the treatment or inhibition of retinopathy of prematurity.

BRIEF DESCRIPTION OF THE DRAWINGS

The invention, and embodiments of apparatus embodying it, will be further described, by way of example, with reference to the drawings, in which.

DETAILED DESCRIPTION OF THE INVENTION

Figure 1:
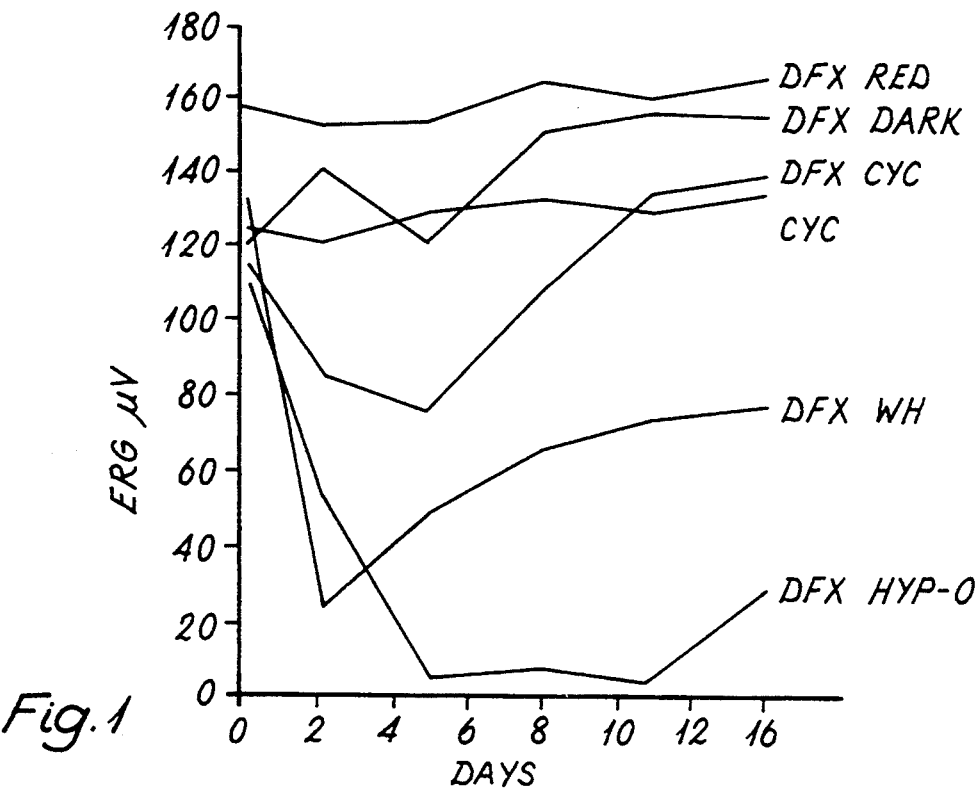
FIG. 1 is a graph showing the effect of various light treatments on rats dosed with DFX.
Figure 2:
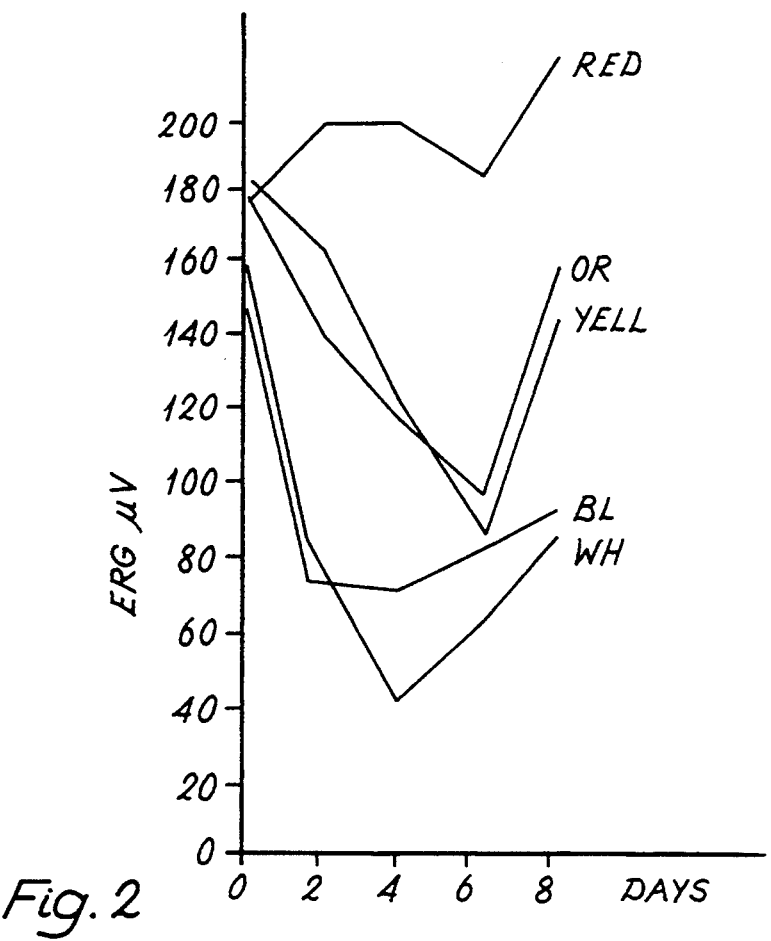
FIG. 2 is a graph showing the effect of various light treatments on dark-adapted albino rats.

FIGS. 1 and 2 show experimental results obtained from rats. The rats were albino Wister rats aged 4–6 weeks, their ERG readings being measured at 2 day intervals.

FIG. 1 shows the results of dosing the rats with DFX (DFX graphs) and subjecting them to various lighting regimes: RED is red light, DARK is darkness, CYC is cyclic white light, and WH is continuous white light. It will be seen that the ERG reading generally falls sharply over 2–4 days, and then rises back towards normal. However, it will be particularly noted that the continuous red light regime holds the ERG reading substantially constant. Thus that regime inhibits the reduction of the EWRG reading which occurs even with the continuous dark regime, and particularly with the other regimes. (The DRX HYP-O graph shows the effect of a high oxygen level as well).

FIG. 2 shows the results of subjecting dark-adapted rats to continuous lighting of various colours: RED is red, OR orange, BL is blue, and WH its white. It will be seen that blue and white light both produce very large ERG reading reductions, with only gradual recovery, while orange and yellow produce large but more gradual reductions with more rapid recovery. It will be noted that red, however, produces no reduction at all, on the contrary, it produces an appreciable increase of the ERG reading.

These results both indicate that the use of red light has a positively beneficial effect, compared to darkness. We believe that the use of this red light for premature babies—that is, the treatment of premature babies in such a way that they are exposed to such light but substantially shielded from light of other colours—will have a beneficial effect in inhibiting the onset of ROP and/or in alleviating its effects.

Figure 3:
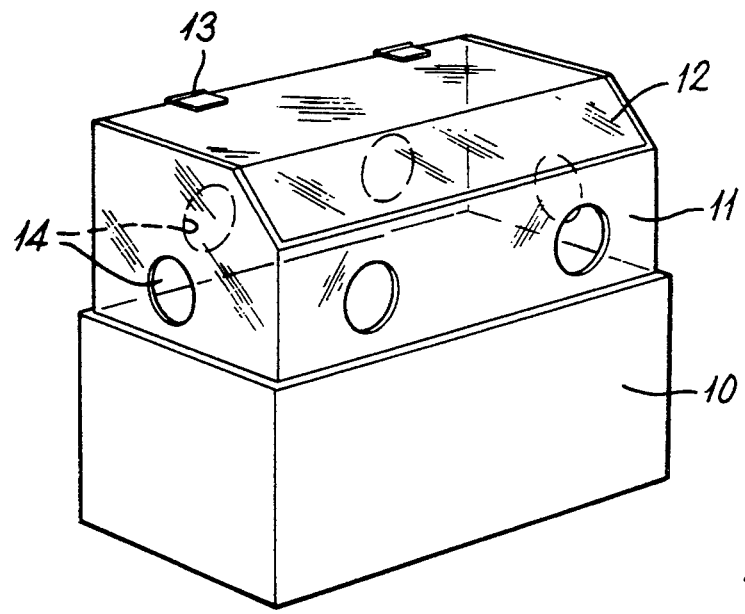
FIG. 3 is a diagrammatic view of an incubator.

FIG. 3 shows an incubator diagrammatically. It consists of a base 10 having a non-opaque hood 11, the hood having a lid 12 hinged at 13. The incubator also has climate control means (not shown) for sensing the conditions (e.g. humidity, temperature, and possibly oxygen concentration) in the incubator and maintaining them at desired levels. The baby is placed on a mattress (not shown) located on the base 10 under the hood 11. The hood 11 has a plurality of access ports 14 spaced around its sides, each closed by a flexible sheet with a hole with an elasticated edge. For present purposes, substantially the whole body of the hood 11 is either made of plastics material which is transparent only to red light (with a cut-off at approximately 612 nm or longer) or is coated with filter material with that transparency, and with the closures of the access ports 14 either having a similar cut-off wavelength or being opaque.

Figure 4:
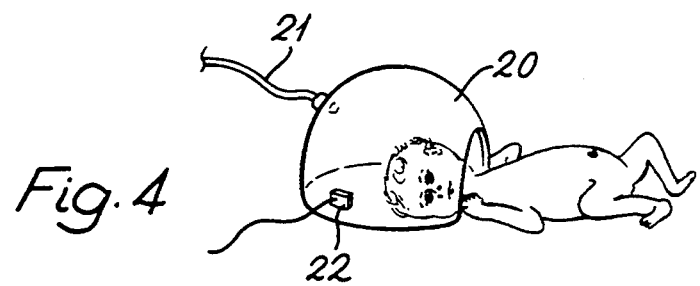
FIG. 4 is a diagrammatic view of a headbox.

FIG. 4 shows a head-box, which is usually used in an incubator and placed over the baby's head as shown, to maintain a local high oxygen level. The headbox 20 has a humidified oxygen inlet 21 and an oxygen level sensor 22. For present purposes, substantially the whole body of the headbox 20 is either made of plastics material which is transparent only to red light (with a cut-off at approximately 612 nm or longer) or is coated with filter material with that transparency. Such a headbox can of course be used in an ordinary incubator, but if an ordinary incubator is used, the headbox would have to be in substantially permanent use (until the danger of ROP was past).

Figure 5:
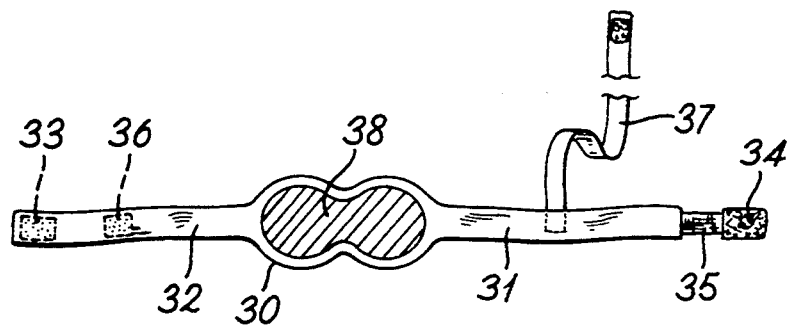
FIG. 5 is a diagrammatic view of an eye protector.

FIG. 5 shows an eye protector. A strip of opaque material has a central eye-covering portion 30, typically some 7–8 cm long, formed integrally with two wings 31 and 32, each typically 11 cm long. Wing 32 has a patch of Velcro (RTM) material 33 attached near its end, and wing 31 has a co-operating strip of material 34 (typically 4 cm long) attached to its end by a strip of elastic material (typically spacing the strip 34 from the wing 31 by 2 cm). The wing 32 has a second patch of Velcro material 36 attached as shown, and a headband 37 (typically 27 cm long) is attached to the wing 31 as shown. The eye-covering portion 30 has a central portion 38 of plastics material which is transparent only to red light (with a cut-off at approximately 612 nm or longer) or is coated with filter material with that transparency; the remainder of the strip 30-31-32 is of opaque material.

The eye protector is used by having its eye-covering portion 30 placed over the eyes of the baby, and secured in place by having the wings 31 and 32 passed round to the back of the baby's head and attached to each other there, with the headband being taken over the top of the baby's head and attached to the patch 36. It needs to be in place substantially permanently (until the danger of ROP is past).

The main body of the strip 30-31-32 may be made of two layers of white cotton or similar material, coated on the meeting faces with an opaque sealing substance. The patches 33 and 36, the elastic 35, and the headband 37 may be sewn to one of these layers before assembly. The plastic material portion 38 may be formed of flat plastics material which is heat pressed to have a pair of connected convex bulges surrounded by a flat rim. To assemble the protector, one layer of the strip 30-31-32 is placed with its sealing-substance side upwards, the portion 38 is placed on it, the second layer of the strip is placed over the first strip and the portion 38 with its sealing-substance side downwards, and the assembly is placed in a heat press which seals the two layers to each other and to the rim of the portion 38.

The two layers of the main body of the strip 30-3-1-32, the portion 38, and the strip itself after assembly may all be shaped partly or wholly by a press with suitable cutting moulds.

We claim:

1. An apparatus for the treatment of or the inhibition of retinopathy of prematurity, comprising:
    means for providing substantially only red light in a wave band of at least about 612 nm; and
    means for receiving at least the head of a baby and for limiting light which reaches the baby's eyes to substantially only said red light.

2. An apparatus accordingly to claim 1, wherein said means for providing red light comprises a light source.

3. An apparatus according to claim 1, wherein said means for providing red light includes means for filtering light.

4. An apparatus according to claim 3, wherein said light filtering means is incorporated in an eye protector.

5. An apparatus according to any one of claims 1-3, wherein said means for receiving comprises an incubator.

6. An apparatus according to any one of claim 1-3, wherein said means for receiving comprises a head box.

7. An apparatus according to claim 2, wherein said light source comprises means for producing substantially only red light.

8. An apparatus according to claim 5, wherein said incubator comprises translucent portions for providing substantially only red light.

9. An apparatus according to claim 6, wherein said head box comprises translucent portions for providing substantially only red light.

10. A method for the inhibition of or treatment of retinopathy of prematurity which comprises:
    providing means for providing substantially only red light in a wave band of at least about 612 mn,
    providing means for receiving at least the head of a baby and for limiting light which reaches the baby's eyes to substantially only said red light;
    placing at least the head of a baby in said means for receiving; and
    providing said red light whereby the baby is allowed to see substantially only red light.

* * * * *